(12) United States Patent
Steinle et al.

(10) Patent No.: US 10,973,587 B2
(45) Date of Patent: Apr. 13, 2021

(54) REFERENCE ARRAY HOLDER

(71) Applicant: Brainlab AG, Munich (DE)

(72) Inventors: Wolfgang Steinle, Munich (DE);
Christoffer Hamilton, Aschheim (DE);
Nils Frielinghaus, Heimstetten (DE)

(73) Assignee: BRAINLAB AG, Munich (DE)

( * ) Notice: Subject to any disclaimer, the term of this patent is extended or adjusted under 35 U.S.C. 154(b) by 319 days.

(21) Appl. No.: 15/752,927

(22) PCT Filed: Aug. 19, 2015

(86) PCT No.: PCT/EP2015/069037
§ 371 (c)(1),
(2) Date: Feb. 15, 2018

(87) PCT Pub. No.: WO2017/028916
PCT Pub. Date: Feb. 23, 2017

(65) Prior Publication Data
US 2018/0235710 A1    Aug. 23, 2018

(51) Int. Cl.
*A61B 34/20*     (2016.01)
*B25J 9/16*      (2006.01)
(Continued)

(52) U.S. Cl.
CPC ............. *A61B 34/20* (2016.02); *A61B 34/10* (2016.02); *A61B 34/30* (2016.02); *A61B 90/37* (2016.02);
(Continued)

(58) Field of Classification Search
CPC . A61B 34/20; A61B 34/30; A61B 2034/2055; A61B 2034/2065;
(Continued)

(56) References Cited

U.S. PATENT DOCUMENTS 5,544,282 A   8/1996 Chen et al.
6,546,277 B1  4/2003 Franck et al.
(Continued)

FOREIGN PATENT DOCUMENTS

EP    0335314 A2   10/1989
EP    1935365 A1   6/2008
(Continued)

OTHER PUBLICATIONS

European Search Report and Written Opinion for corresponding PCT/EP2015/069037, 17 pages, dated Apr. 20, 2016, NL.

*Primary Examiner* — Spencer D Patton
(74) *Attorney, Agent, or Firm* — Tucker Ellis LLP (57) ABSTRACT

Provided is a reference array holder, including a first segment configured to be mounted to a reference structure, and a second segment supporting a reference array having at least one tracking marker, wherein the second segment is movably coupled to the first segment via at least one coupling, and wherein the at least one coupling includes a sensor that provides information as to the spatial position of the second segment relative to the first segment. Also provided is tracking and/or navigation system including such reference array holder and to a computer implemented method of controlling a reference array holder.

10 Claims, 3 Drawing Sheets

(51) Int. Cl.
*A61B 34/10* (2016.01)
*A61B 34/30* (2016.01)
*A61B 90/00* (2016.01)
*A61B 90/50* (2016.01)
*G06T 7/70* (2017.01)
*G06T 7/00* (2017.01)
*G06T 11/00* (2006.01)
*A61N 5/10* (2006.01)

(52) U.S. Cl.
CPC ............ A61B 90/50 (2016.02); B25J 9/1666 (2013.01); B25J 9/1676 (2013.01); G06T 7/0012 (2013.01); G06T 7/70 (2017.01); G06T 11/001 (2013.01); *A61B 2034/105* (2016.02); *A61B 2034/107* (2016.02); *A61B 2034/2055* (2016.02); *A61B 2090/364* (2016.02); *A61B 2090/365* (2016.02); *A61N 5/1049* (2013.01); *A61N 2005/1059* (2013.01); *G06T 2207/10024* (2013.01); *G06T 2207/10028* (2013.01); *G06T 2207/10081* (2013.01); *G06T 2207/10088* (2013.01); *G06T 2207/30024* (2013.01); *G06T 2207/30241* (2013.01)

(58) Field of Classification Search
CPC ............ A61B 2034/2068; B25J 9/1666; B25J 9/1674; B25J 9/1676; B25J 9/1692; B25J 9/1694; B25J 9/1697; B25J 19/021; B25J 19/023; G05B 2219/39016; G05B 2219/39024; G05B 2219/39057; G05B 2219/39008; G05B 2219/39011; G05B 2219/39039; G05B 2219/39042; G05B 2219/39045; G05B 2219/39046; G05B 2219/39387; G05B 2219/39391; G05B 2219/39393

See application file for complete search history.

(56) References Cited

U.S. PATENT DOCUMENTS

| | | | |
|---|---|---|---|
| 8,571,710 | B2 | 10/2013 | Coste-Maniere et al. |
| 2003/0109780 | A1 | 6/2003 | Coste-Maniere et al. |
| 2009/0259230 | A1 | 10/2009 | Khadem et al. |
| 2010/0168763 | A1 | 1/2010 | Zhao et al. |
| 2011/0028992 | A1* | 2/2011 | Geiger .................. B25J 9/1664 606/130 |
| 2012/0060847 | A1 | 3/2012 | Stratton et al. |
| 2012/0320186 | A1* | 12/2012 | Urban ................ A61B 1/00149 348/79 |
| 2013/0313382 | A1* | 11/2013 | Jakubczak ............ A61B 90/50 248/124.1 |
| 2015/0031985 | A1 | 1/2015 | Reddy et al. |

FOREIGN PATENT DOCUMENTS

| | | |
|---|---|---|
| WO | 2015147798 A1 | 10/1989 |
| WO | 9610368 A2 | 4/1996 |
| WO | 2008130355 A1 | 10/2008 |
| WO | 2010140074 A1 | 12/2010 |
| WO | 2013192598 A1 | 12/2013 |
| WO | 2014019714 A2 | 2/2014 |
| WO | 2014139024 A1 | 9/2014 |

* cited by examiner

REFERENCE ARRAY HOLDER

The present invention relates to a reference array holder used for medical purposes, a corresponding tracking and/or navigation system, and a computer implemented method of controlling such reference array holder.

In medical procedures such as image-guided surgery (IGS) or radiotherapy, it is desirable to have a reference array to which a medical tracking and navigation system can refer when determining the position and/or alignment of objects within an operational field. It is then possible to determine the position and/or adjustment of any tracked object as well as the position and/or alignment of any tracked objects relative to each other by determining the relative position and/or alignment of the tracked objects with respect to the reference array. Such reference has to have a substantially invariant position and alignment within the operational field.

For determining its spatial position and alignment, the reference array may, as any other object tracked by the tracking system, be provided with tracking markers configured to be recognized by the tracking system.

The reference structure may be any object or structure that maintains its position and alignment within the operational field, for example an operating table or any structure that is at least semi-rigidly fixed to the operating table.

The term reference array usually refers to a device with a number of markers, advantageously three markers, attached to it, wherein the markers are (for example detachably) attached to the reference array such that they are stationary, thus providing a known (and advantageously fixed) position of the markers relative to each other. The position of the markers relative to each other can be individually different for each reference array used within the framework of a surgical navigation method, in order to enable a surgical navigation system to identify the corresponding reference array on the basis of the position of its markers relative to each other. It is therefore also then possible for the objects to which the reference array is attached to be identified and/or differentiated accordingly. In a surgical navigation method, the reference array serves to attach a plurality of markers to an object (for example, a patient couch or any other structure that is at least semi-rigidly fixed within the operating area) in order to be able to detect the position of the object (i.e. its spatial location and/or alignment). Such a reference array for example features a way of being attached to the object (for example, a clamp and/or a thread) and/or a holding element which ensures a distance between the markers and the object (for example in order to assist the visibility of the markers to a tracking marker and/or navigation system) and/or marker holders which are mechanically connected to the holding element and which the markers can be attached to.

The markers of the reference array can be of any suitable type that corresponds to the type of the tracking system used. For example, passive retro-reflective markers may be provided as well as active light-emitting markers for a tracking system that comprises optical cameras configured to detect the markers. However, it is also conceivable that electro-magnetic (EM)-markers or even ultrasound markers are provided for an EM-tracking system or an ultrasound tracking system, respectively.

Known reference arrays for optical navigation are permanently positioned in the operational field and it is known that accuracy of a navigation procedure increases with the size of the reference array.

The present invention has realized that surgical procedures in particular can be improved by providing a reference array in its operational position only for time periods the reference array is actually needed for navigation purposes, and that the accuracy of the navigation can further be increased by providing an even larger reference array which would compromise mobility during a surgical procedure if it was installed permanently within the operational field.

The reference array holder, the system and the method are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

According to the present invention, the inventive reference array holder comprises a first segment configured to be mounted to a reference structure, and a second segment supporting a reference array having at least one tracking marker, wherein the second segment is movably coupled to the first segment via at least one coupling, and wherein the at least one coupling comprises a sensor that provides information as to the spatial position of the second segment relative to the first segment.

In other words, the inventive reference array holder comprises two segments movably coupled to each other, such that the reference array can be moved relative to the reference structure. At least one sensor is used to determine the relative position of the two segments and consequently the position of the reference array relative to the reference structure. This enables the reference array to be moved "out of the way" when it is not needed for navigation purposes, so that the spatial volume normally occupied by the reference array can be used otherwise.

The reference array holder may comprise, along with the first and the second segment, at least one further segment, wherein the first segment, the second segment and the at least one further segment may be coupled to each other in sequence via a plurality of couplings. With an increasing number of segments, "flexibility" of the reference array holder increases, as the number of possible positions the reference array can be moved into increases.

Further, it is conceivable that the at least one sensor which is configured to provide information as to the spatial position of the segments is assigned to a coupling that movably connects two adjacent segments. The sensor may then determine the relative position of the two adjacent segments connected to each other via the corresponding couplings.

For example, a sensor assigned to a coupling may be a photoelectric sensor that can comprise photodiodes and an opaque disk that has several through-holes which allow light to pass the disk, so that the holes in the disk are recognized by the photodiodes. In the alternative, the sensor may be an inductive sensor which provides information as to the relative position by means of receiver-coils. Of course, any other suitable type of sensor is conceivable for being assigned to a coupling between two segments of the reference array holder. In principle, the sensor does not even have to be a sensor assigned to or accommodated within a coupling, but may be for example an "external" sensor that may even be spaced apart from the reference array holder, and is configured to detect the relative position of the reference array holder segments, for example by an optical recognition.

Further, any type of coupling connecting two adjacent segments, that provides at least one and up to three translational and/or rotational degrees of freedom may be used in the scope of the present invention. For example, at least one coupling may provide one single translational degree of freedom, such that the two adjacent segments may be moved relative to each other in a telescope-like manner. Further, at least one coupling may take the form of a ball-joint providing three rotational degrees of freedom. Further, at least one coupling may be a pivot-joint, providing one single rotational degree of freedom.

All of the sensors described above allow determining the spatial position and/or alignment of the reference arrays operational position and/or alignment. Further, the relative movement within each of the couplings is known which was performed to move the reference array from the operational position into a parking position, away from the operational field. It is therefore possible to reconstruct the inverse movement within each coupling that is necessary to reobtain the original operational position and/or alignment of the reference array.

Specifically, user-guidance may be provided, informing the user which of the couplings has to be moved in which manner so as to reobtain the initial operational position that is necessary to continue with IGS at any desired point in time.

Additionally or alternatively to the "manual" manipulation of the reference array holder by medical personnel, an "automatic" actuation of at least one coupling is conceivable by providing at least one of the couplings with an actuator that is configured to move two adjacent segments relative to each other. Such actuator may be provided with the necessary information obtained by a corresponding sensor that allows the actuator to return into its original position at any desired point in time.

The reference array holder may also be responsive to a control signal transmitted by a control unit, the control signal causing the reference array holder to move the reference array relative to the reference structure. This will allow the reference array holder to act fully automatically in response to a certain situation within the operational field.

For example, the tracking and/or navigation system, or the reference array holder in particular may comprise a sensor which detects the presence of objects in the vicinity of the reference array. In case an object is detected within a predetermined spatial volume around the reference array, the reference array holder may be controlled to move the reference array out of the operational position and into a parking position, for example. This not only allows avoiding unintended contact of objects or persons with the reference array, which might be detrimental to navigation accuracy. It is also possible to "push" the reference array out of the operation field without contact, in case the reference array is not needed any more for navigation purposes. Specifically, any optical or acoustical sensor is considered suitable for this purpose.

Further, at least one operational position, at least one parking position and/or at least one functional position may be provided for the reference array, which can be moved between these positions. For example, an operational position may be a predefined and invariant position for the reference array, but may also be individually defined by medical personnel prior to a registration procedure. Further, at least one parking position may be predefined, i.e. a recommended position for which the reference array is supposed to have least influence on mobility within the operational field. At least one parking position may also be individually defined depending on the preferences of the medical personnel. At least one parking position may even depend on a present or future situation sensed by the control unit. For example, different procedural steps may require different parking positions for the reference array, so that the control unit, depending on the present or an oncoming procedural step, may set the parking position for the reference array. Further, at least one functional position may be provided, for example, a functional position which facilitates draping of the reference array and/or the reference array holder with a surgical drape, or a functional position that facilitates replacing a detachable reference array by another, for example bigger reference array, or a reference array with another geometry. Further functional positions may be provided for cleaning or replacing tracking markers, cleaning the reference array holder, mounting or dismounting the reference array holder to or from a reference structure, checking accuracy of the reference array holder, or calibrating tracked instruments with the help of the reference array.

It is also conceivable that at least one parking position and/or at least one functional position is/are variable and may in particular depend on the relative position of the reference array moving objects recognized by the tracking system. For example, in case a parking position or a functional position the reference array would be transferred to is currently occupied by another object, another available parking position or functional position can be chosen. At least one parking position and/or functional position may even be somehow "dynamic": For example, the reference array may give way to another object approaching the reference array in its current position, thereby avoiding any contact with objects. However, in certain circumstances, contact with another object or person may even be intended: For example the reference array may move from an operational position to a parking position or to a functional position, or vice versa when being touched by an object or person.

Further, the reference array holder may even be responsive to a situation involving the position and/or properties of objects and/or subjects in the operating field, wherein at least one parking position and/or at least one functional position depends on that situation. For example, in case a certain object approaches the operating field or enters the operating room (for example a mobile CT scanner) the reference array may automatically move into a parking position for an oncoming imaging procedure.

The present invention further relates to a computer implemented method of controlling a reference array holder as described herein, wherein the method comprises the steps of:
  acquiring requirement data describing at least one situation that requires the reference array to move from an operational position to a parking position or to a functional position, or vice-versa;
  acquiring situation data describing an actual situation involving the current spatial position of said reference array;
  determining, based on a comparison of said requirement data and said situation data, control data describing a necessity of a motion of the reference array.

As a first step, possible situations are defined which would require the reference array to move from its current position. As a second step, the situation, for example a present or a future situation within the operating field is determined, for example by means of sensors or a user input, whereupon it is decided whether it is necessary for the reference array to move from its current position into another position.

As already mentioned above, medical personnel may input a definitive command, for example via a machine-user interface such as a touchscreen or via voice control, to have the reference array to leave its current position.

Said situation data may comprise information as to:
- an object or subject approaching the reference array;
- a position and/or presence of an object or subject tracked by a medical tracking system;
- a current or imminent procedural step of a medical procedure;
- a contact of the reference array or the reference array holder; and/or
- a force acting on the reference array or the reference array holder.

The present invention further relates to a program, which when running on a computer causes the computer to perform the method steps of the method as described herein and/or a program storage medium on which the program is stored, particularly in a non-transitory form. Further, the present invention relates to a medical tracking and/or navigation system, comprising a computer on which such program is stored and/or run.

The method in accordance with the invention is for example a computer implemented method. For example, all the steps or merely some of the steps (i.e. less than the total number of steps) of the method in accordance with the invention can be executed by a computer. An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired.

The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:

the computer of the preceding claim, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
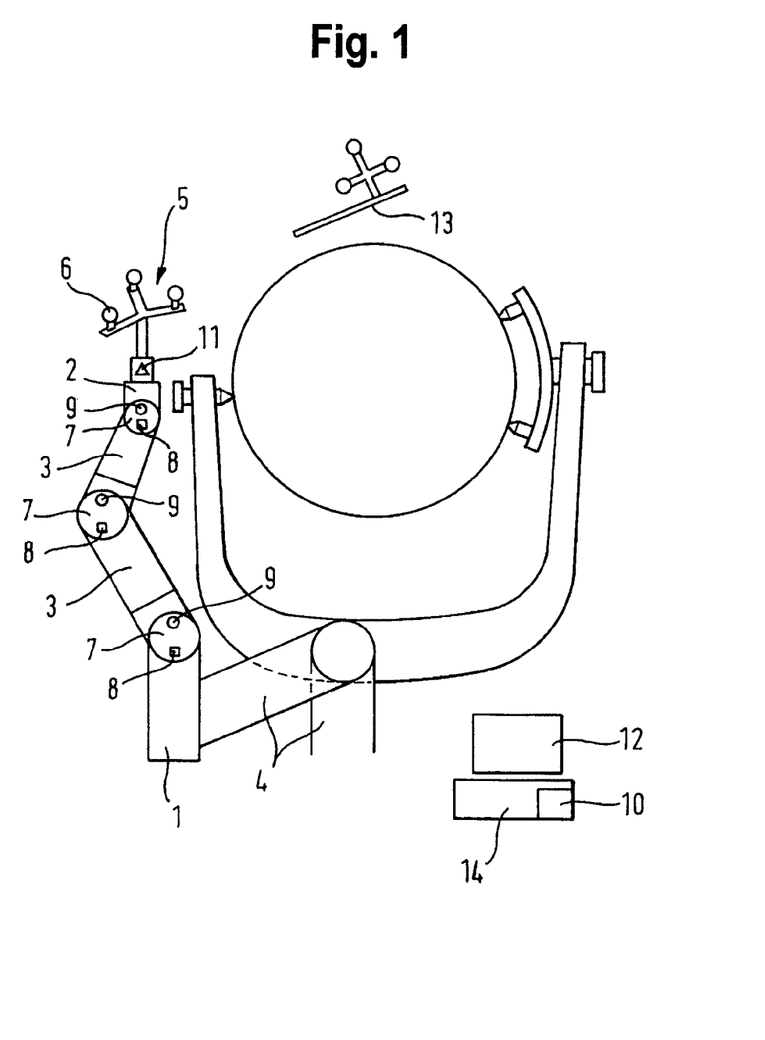
FIG. 1 shows an articulated reference array holder according to the present invention in an operational position.

FIG. 1 shows an articulated reference array holder according to the present invention, which comprises four segments 1, 2 and 3, which are connected to each other in sequence via three pivot joints 7, each of the joints providing one rotational degree of freedom. A further rotational degree of freedom around the longitudinal axis of the reference array holder may be provided by a rotational mount (not shown) connecting the first segment 1 to the reference structure 4. In this case, the reference structure 4 is fixedly attached to an operating table. Each of the pivot joints 7 comprises one sensor 8 sensing the relative position of the respective segments 1, 2 and 3 connected by the corresponding coupling 7. Further, each coupling 7 comprises an actuator 9 which is configured to move the two adjacent segments 1, 2 and 3 coupled to each other via the corresponding coupling 7. The top segment 2 releasable supports reference array 5 which comprises three optical marker spheres 6, which are configured to be recognized by optical cameras or by a medical tracking and/or navigation system. The top segment 2 further comprises a sensor 11 which detects the presence of objects in the vicinity of the reference array 5, so that an unintended contact with those objects, for example a tracked pointer instrument 13 can be avoided.

Further, a computer 14 is provided, which comprises a control unit 10 and a touch-screen 12 serving as machine-user interface, which is to control the articulated reference array holder.

Figure 2:
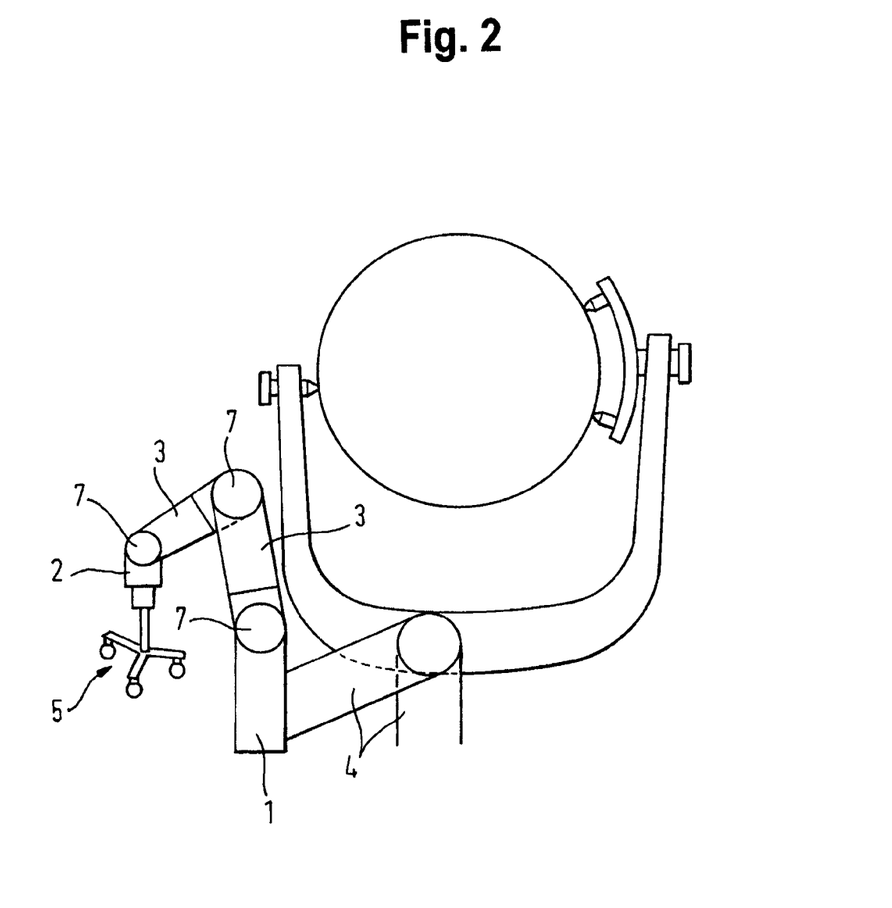
FIG. 2 shows an articulated reference array holder according to the present invention in a parking position.
Figure 3:
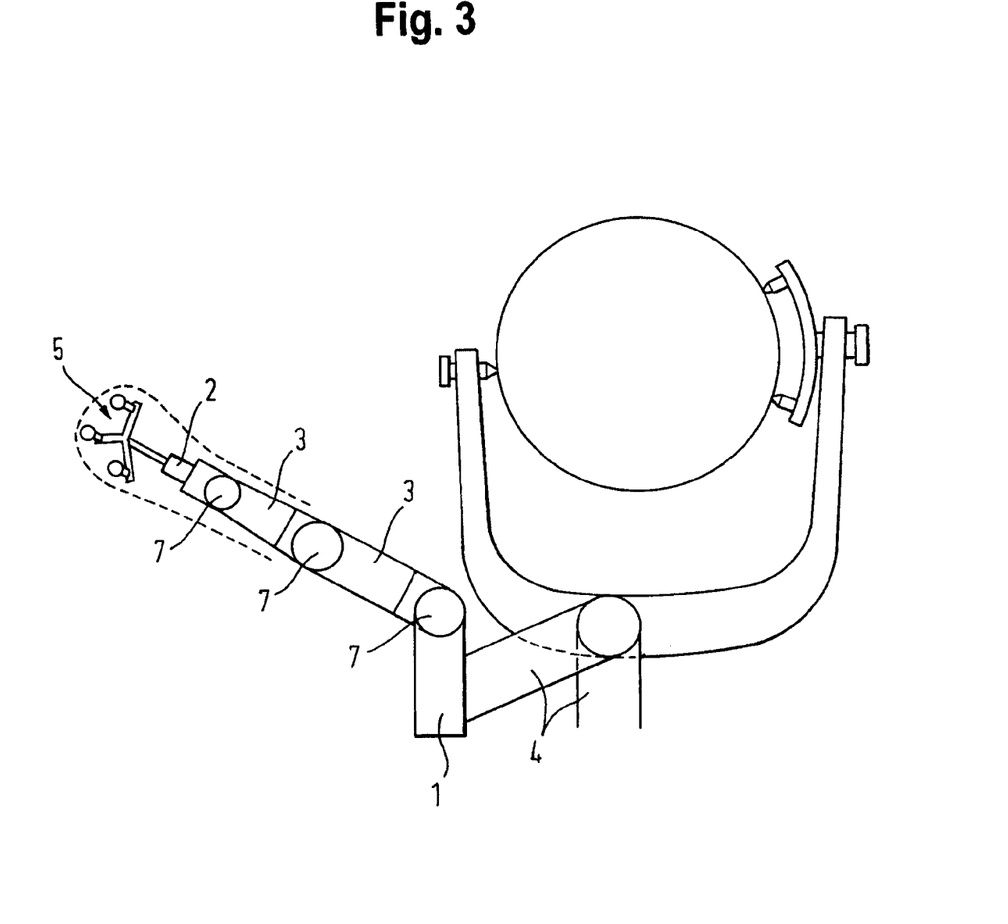
FIG. 3 shows an articulated reference array holder according to the present invention in a functional position.

FIGS. 2 and 3 show the reference array holder of FIG. 1 in a parking position away from the operational field in the vicinity of the patient's head, and in a functional position, respectively, in which the reference array holder stretches away from the operational field in a straight manner, so that a drape (shown in broken lines) can be drawn over the reference array 5 and the reference array holder.

The invention claimed is:

1. A reference array holder comprising:
   a first segment configured to be mounted to a reference structure;
   a second segment supporting a reference array having at least one tracking marker, the second segment being movably coupled to the first segment via at least one coupling;
   the at least one coupling comprising an actuator configured to move the first and second segments relative to each other and a sensor that provides information as to the spatial position of the second segment relative to the first segment; and
   a control unit configured to transmit a control signal causing the reference array holder to move the reference array relative to the reference structure from an operational position within an operational field into a predefined parking position away from the operational field or a predefined functional position away from the operational field, and from the predefined parking position away from the operational field or the predefined functional position away from the operational field back into the operational position within the operational field,
   wherein the control signal is transmitted depending on a presence of one or more objects in the operational field, the presence being recognized by a medical tracking system.

2. The reference array holder according to claim 1, further comprising at least one further segment, wherein the first segment, the second segment and the at least one further segment are coupled to each other in sequence via a plurality of couplings.

3. The reference array holder according to claim 1, wherein at least one of the couplings comprises a sensor that determines the relative position of two adjacent segments connected to each other by the coupling.

4. The reference array holder according to claim 1, wherein at least one coupling rotatably connects two adjacent segments.

5. The reference array holder according to claim 1, further comprising a sensor that detects the presence of objects in the vicinity of the reference array.

6. The reference array holder according to claim 1, wherein the predefined parking position and/or the predefined functional position depends on a situation involving the position and/or properties of objects and/or subjects in the operational field.

7. A computer implemented method of controlling a reference array holder comprising a first segment configured to be mounted to a reference structure, a second segment supporting a reference array having at least one tracking marker, the second segment being movably coupled to the first segment via at least one coupling, the at least one coupling comprising an actuator configured to move the first and second segments relative to each other and a sensor that provides information as to the spatial position of the second segment relative to the first segment, and a control unit configured to transmit a control signal causing the reference array holder to move the reference array relative to the reference structure back into an operational position within an operational field after the reference array has been moved from the operational position, the method comprising the steps of:

acquiring requirement data describing at least one situation that requires the reference array to move from an operational position within the operational field to a predefined parking position away from the operational field or to a predefined functional position away from the operational field, and vice-versa;

acquiring situation data describing an actual situation involving a presence of one or more objects in the operational field, the presence being recognized by a medical tracking system;

determining, based on a comparison of said requirement data and said situation data, control data describing a necessity of a motion of the reference array; and controlling the actuator based on the control data.

8. The method according to claim 7, wherein said control data is output via a machine-user interface, or is transmitted to a control unit controlling said at least one actuator.

9. The method according to claim 7, wherein said situation data comprises information as to:

an object or subject approaching the reference array;

a position and/or presence of an object or subject tracked by a medical tracking system;

a current or imminent procedural step of a medical procedure;

a contact of the reference array or the reference array holder; and/or a force acting on the reference array or the reference array holder.

10. A non-transitory computer readable storage medium storing a program which, when running on a computer or loaded onto the computer, causes the computer to:

acquire requirement data describing at least one situation that requires a reference array to move from an operational position within an operational field to a predefined parking position away from the operational field or to a predefined functional position away from the operational field, and vice-versa;

acquire situation data describing an actual situation involving a presence of one or more objects in the operational field, the presence being recognized by a medical tracking system;

determine, based on a comparison of said requirement data and said situation data, control data describing a necessity of a motion of the reference array; and control an actuator included within the array based on the control data, wherein the reference array is operably connected to the computer and comprises a reference array holder comprising a first segment configured to be mounted to a reference structure, a second segment supporting the reference array having at least one tracking marker, the second segment being movably coupled to the first segment via at least one coupling, the at least one coupling comprising the actuator configured to move the first and second segments relative to each other and a sensor that provides information as to the spatial position of the second segment relative to the first segment, and a control unit configured to transmit a control signal causing the reference array holder to move the reference array relative to the reference structure back into an operational position within the operational field after the reference array has been moved from the operational position.

* * * * *